United States Patent [19]

Hewson et al.

[11] Patent Number: 4,574,807
[45] Date of Patent: Mar. 11, 1986

[54] METHOD AND APPARATUS FOR PACING THE HEART EMPLOYING EXTERNAL AND INTERNAL ELECTRODES

[76] Inventors: Carl Hewson, Old Ocean St., Marshfield, Mass. 02050; Paul F. Ridolpho, 1424 Tomasito St., NE., Albuquerque, N. Mex. 87112

[21] Appl. No.: 585,761

[22] Filed: Mar. 2, 1984

[51] Int. Cl.⁴ ............................................. A61N 1/36
[52] U.S. Cl. ............................. 128/419 PG; 128/786
[58] Field of Search ............ 128/419 D, 419 PG, 715, 128/784, 785, 786

[56] References Cited

U.S. PATENT DOCUMENTS

| | | | |
|---|---|---|---|
| 3,614,955 | 10/1971 | Mirowski et al. | 128/419 D |
| 3,804,098 | 4/1974 | Friedman | 128/786 |
| 4,088,138 | 5/1978 | Diack et al. | 128/419 D |
| 4,161,952 | 7/1979 | Kinney et al. | 128/786 |
| 4,176,660 | 12/1979 | Mylrea et al. | 128/715 |
| 4,198,963 | 4/1980 | Barkalow et al. | 128/419 D |
| 4,351,330 | 9/1982 | Scarberry | 128/419 D |

Primary Examiner—William E. Kamm
Attorney, Agent, or Firm—Wolf, Greenfield & Sacks

[57] ABSTRACT

When a person's heart is beating at a slow or an irregular rate, or after defibrillation, the heart should be stabilized to beat at a particular rate. This electronic pacing method and apparatus can accomplish that purpose without surgery and in a few seconds. It is accomplished by a flexible tube or rod having a series of circumferential electrically conductive rings spaced a few centimeters apart and electrically connected together which may be inserted down the esophagus so as to place the rings in the lower portion thereof. A second electrode which may be a conventional adhesively attached ECG electrode is attached to the sternum. An electrical pulse of short duration and low power which may emanate from a small battery operated electronic stimulator is passed between the electrodes. The pulses stimulate the heart muscles and make the heart beat at a preset rate. The tube or rod with the electrodes may be small enough to pass through an esophageal gastric tube or similar device.

13 Claims, 7 Drawing Figures

METHOD AND APPARATUS FOR PACING THE HEART EMPLOYING EXTERNAL AND INTERNAL ELECTRODES

This invention relates to a method and apparatus for pacing or controlling the heart and, more particularly, comprises an improved method and apparatus for heart pacing which may be used without making any surgical incisions in the patient. Consequently, it makes possible the effective pacing of the human heart so as to achieve continuous heart function at a selected rate, by a paramedic.

At the present time, all known techniques for internal pacing of the heart involve surgery and call for the placement of an electrode to the heart. The different surgical procedures involved, such as cut down of the carotoid vessel, can only be performed by a medical doctor, and are difficult if not impossible, as well as dangerous, to perform outside an operating room. Moreover, all of the known procedures take many minutes during which death of heart muscle may occur.

In accordance with the present invention, one of the two pacer electrodes is applied externally against the chest over the sternum, and the second electrode is inserted into the lower portion of the esophagus. In the preferred form of the invention the internal electrode has several contacts which are placed in the lower third of the esophagus, and any of the contacts may form with the external electrode the conductive path through the heart when a pulsed charge is imposed across the electrodes.

The internal electrode in the esophagus may be inserted through the mouth in the fashion of a gastric tube, and in accordance with the simplest form of this invention, the electrode itself may be of selected stiffness and flexibility so that it can be inserted directly into the esophagus. In accordance with other embodiments of this invention, the pacer is incorporated into an esophageal obturator airway, and the internal electrode is inserted through a larger ventilating member which is first placed in the esophagus. In this more sophisticated embodiment, the internal electrode may actually be incorporated into a gastric tube so that the apparatus may ventilate the lungs, relieve pressure in the lower portion of the esophagus, relieve the gastric contents of the stomach, and pace the heart. All of the embodiments of this invention can be rendered operative in a very short time, whenever the patient is found, and without the aid of a medical doctor.

The invention will be better understood and appreciated from the following detailed description of several embodiments thereof read in connection with the accompanying drawing.

DETAILED DESCRIPTION

Figure 1:
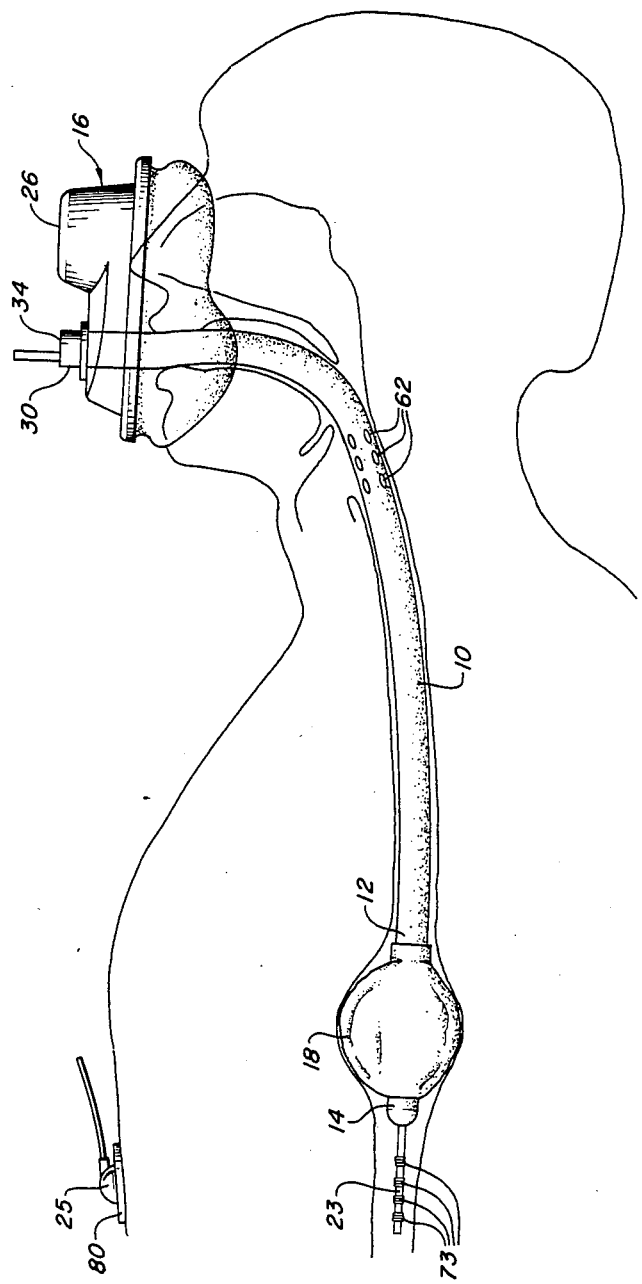
FIG. 1 is a cross-sectional view, somewhat diagrammatic, of the head and chest of a patient and showing one embodiment of the pacer of this invention in place.

The apparatus shown in FIGS. 1-4 includes a main hollow tubular ventilating member 10 closed at its distal end 12 by tip 14, a clear plastic mask 16, an inflatable cuff 18, a relief tube 20, an internal electrode 23 and an external electrode 25, and a pacer circuit 27. The member 10, tip 14, mask 16, cuff 18 and relief tube 20 are the same as shown and described in detail in our copending application Ser. No. 585,764, filed Mar. 2, 1974 entitled apparatus for sealing the esophagus, providing artificial respiration and relieving pressure on distal end of esophagus.

Tubular member 10 is somewhat curved as shown in FIG. 1 to facilitate its insertion through the mouth, over the tongue and into the esophagus of the patient. The tip 14 on the distal end 12 has a rounded or blunt nose that facilitates the insertion of the tube into the esophagus. The tubular member 10 which typically may be made of pvc is somewhat flexible and pliable so that it can conform to the shape of the esophagus. Its length is such that the distal end terminates in the esophagus a few inches below the carina when the device is in place. The proximal end 21 of member 10 terminates at mask 16.

The mask 16 is designed to cover a substantial portion of the patient's face including the nose and mouth. Mask 16 has an inflatable collar 22 that extends about the mask's entire periphery so that the mask may fit tightly against the face of the patient. An inflation tube 24 is provided with appropriate valving to enable the collar 22 to be inflated. The mask also is provided with an enlarged portion 26 to accommodate the patient's nose.

A number of openings are provided in the mask. One opening 28 is occupied by a relatively rigid bite tube 30 that extends an inch or more above the outer surface 32 of mask 16 while its other end extends from inside the mask a sufficient distance to enter the mouth of the patient beyond the teeth when the mask lies against the face. The proximal end of the bite may be a standard connector to connect it to ventilating apparatus. The bite tube 30 prevents the patient from clamping down on it and obstructing flow through the ventilating member 10. The upper end of member 10 fits snugly over the inner end of the bite tube so that the bite tube 30 forms part of the proximal end of member 10. The two cooperate to form a continuous duct from the outer end 34 of the bite tube outside the mask 16 to the tip 14 at the distal end.

A second opening 36 in mask 16 adjacent the opening 28 carries a tubular fitting 38. The inner end of the fitting extends beyond the inner surface 40 of the mask 16 into the proximal end 42 of relief tube 20. The fitting 38 and bite tube 30 are closely adjacent one another in the mask so that the member 10 connected to the bite tube 30 and relief tube 20 connected to fitting 38 both can extend into the patient's mouth when the mask is in place.

Figure 2:
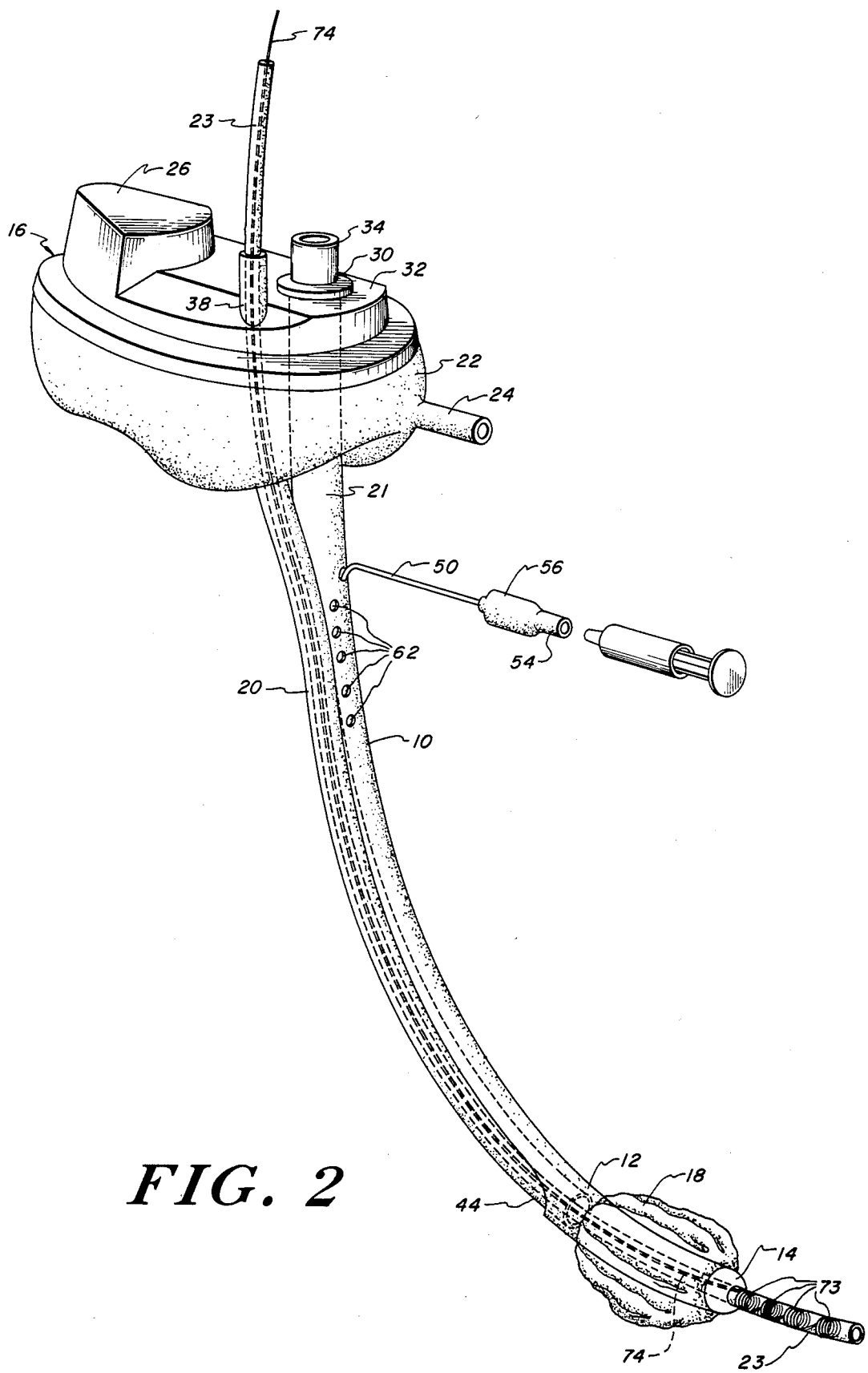
FIG. 2 is a perspective view of the pacer shown in FIG. 1.

In FIG. 2, the relief tube 20 is shown mounted in the wall of member 10 throughout a substantial portion of the length of the member, and on the proximal side of cuff 18, tube 20 enters the member 10 and is fully contained within it. The distal end 44 of tube 20 terminates above tip 14. The surface of the relief tube 20 is cemented to the sides of the opening in the member so that no leakage can occur from member 10 along the sides about the tube 20.

Figure 2A:
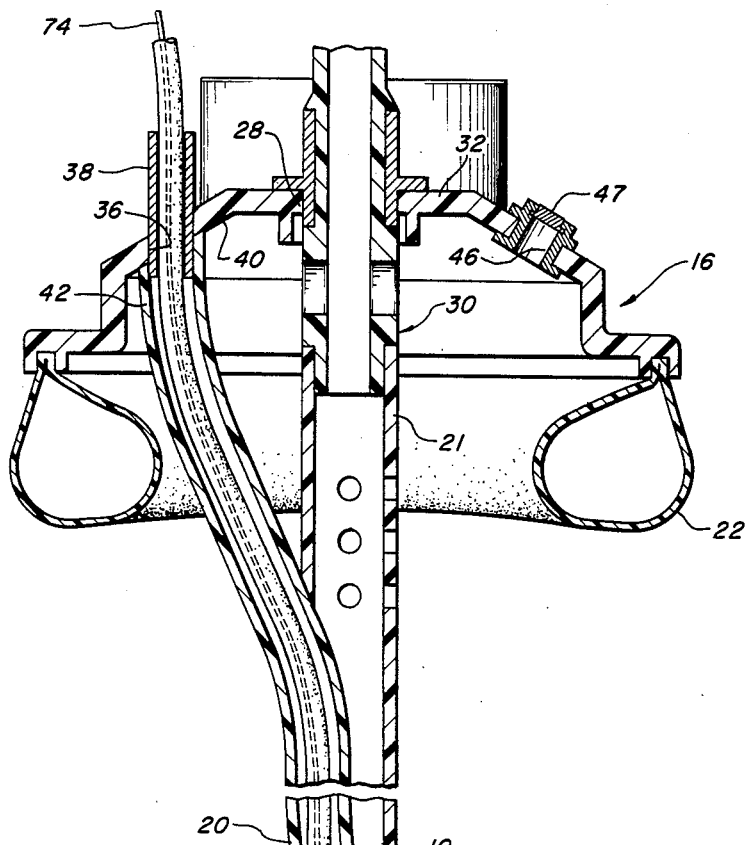
FIG. 2A is a cross-sectional view of the pacer shown in FIG. 2.

A third opening 46 is provided in the mask 16 as shown in FIG. 2A. That opening has a slide cover 47 to enable the opening to be closed when not in use. The opening 46 enables an attendant to insert a suction catheter to draw phlegm and other secretions from the patient's mouth and throat without removing the mask.

In its preferred form, the cuff 18 is made of a highly flexible material such as pvc and when relaxed, it readily collapses. The cuff is connected to a very small diameter tube 50 which may be embedded in or lie against the inner surface of the circumferential wall of member 10. The tube 50 is connected at its inner end to the inside of cuff 18 and provides a passage to enable the cuff to be inflated after the member is in place in the esophagus. The other end of the tube 50 exits from the member 10 below the mask. The tube 50 extends under the inflatable collar 22 of the mask and passes through the mouth of the patient when the device is in place. The outer end of the tube 50 carries a valve 54 and pressure indicator 56, and it is designed to be connected to the inflation member 58. These elements are all well known in the art and need not be described in greater detail.

As is shown in FIGS. 1 and 2, the member 10 at its mid portion has a number of openings 62 through its tubular wall. The openings 62 provide communication between the member 10 and the respiratory passages in the patient's lungs. An attendant may resuscitate the patient typically by attaching the proximal end of the bite tube 30 to a ventilating machine or by breathing into the member 10 through the bite tube 30. The ventilating gas will pass through the bite tube, into member 10, and out the openings 62 to the patient's respiratory passages. Openings may be provided in the bite tube to supplement the opening 62 during exhalation, and the cuff 18 may serve to monitor cardio pulminary resuscitation, all as more fully described in our copending application, supra.

Resuscitation is frequently accompanied by a rapid build-up of pressure in the stomach and the lower third of the esophagus, and if that pressure is not relieved, rupture of the esophagus is possible. The relief tube 20 is provided to relieve that pressure and thereby avoid the life-threatening risk. In addition, any stomach discharge caused by vomiting may exit through passage 20 and fitting 38 to a point outside the mask.

The apparatus described above, absent the electrodes 23 and 25 and circuit 27, is used for ventilating the patient as follows:

With the cuff 18 fully deflated, the member 10 and the relief tube 20 are inserted into the patient's mouth and over the tongue into the esophagus. The length of the member 10 is such that when the inflated collar 22 of the mask contacts the patient's face, the cuff 18 lies a few inches below the carina, that is, well below the location where the trachea divides to the lungs. The collar 22 forms a seal against the face. The cuff 18 is then inflated by means of the pump 58. The pressure in the cuff may be observed by the expansion of the pressure indicator 56 in the well-known manner. Valve 54 enables the tube 50 to be closed after the cuff 18 is inflated so as to prevent cuff deflation. The expanded cuff 18 lies against the inside of the esophagus to seal the upper two thirds of the esophagus from the stomach and prevents any of the stomach contents from rising in the esophagus and entering the patient's respiratory passages. With the member 10 in place in the esophagus and the mask 60 against the face, and with the cuff 18 inflated, ventilating gas provided by the attendant enters the member 10 and flows through the openings 62 to the patient's respiratory passages.

The relief tube 20 is available to relieve the pressure in the lower third of the esophagus and the stomach. However, the stomach contents cannot be aspirated through the esophagus into the patient's mouth and throat passages with consequent gastric spillage into the respiratory passages.

Figure 3:
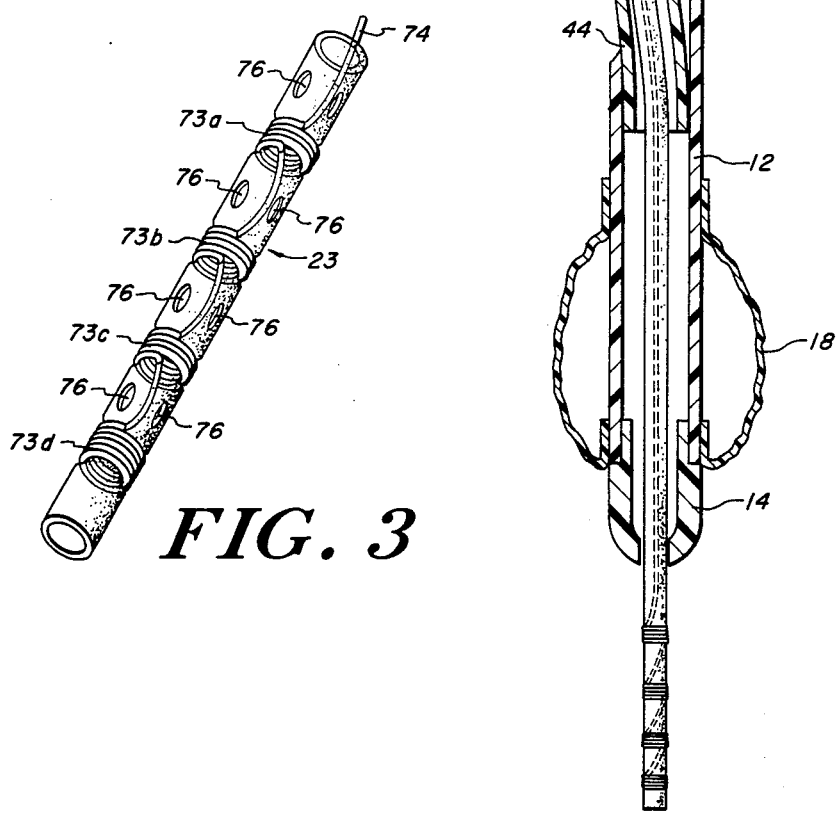
FIG. 3 is an enlarged perspective view of the distal end of the internal electrode forming part of the embodiment of FIGS. 1-2A.

In FIGS. 1–4, the electrode 23 made of a thin flexible tube is shown to extend through fitting 38 in mask 16 and the entire length of the relief tube 20 and out opening 60 in tip 14. In FIG. 3, the electrode 23 is shown to include four contact rings 73 at its distal end 72 embedded in its surface. While four rings are shown, a lesser or greater number may be used. In this embodiment the electrode 23 is a small diameter tubular member, and the four contact rings are formed from a continuous length of tinned copper wire 74 which is connected to post contact 75 at the proximal end of the electrode 23. The wire extends inside the tube to first ring contact 73a in turn formed by several turns of the wire on the surface of the tube. The wire again enters the tube beyond the contact 73a and reemerges at the next ring contact 73b also formed by several additional turns of the wire. The third and fourth ring contacts 73c and 73d are similarly formed and connected to the contact 73b by the wire inside the tube. Thus the four electrode contacts are connected in series from the single length of wire. Typically, each of the ring contacts may be 0.2 inch in length and they may be spaced one inch apart. The wire may typically be 24 gauge. In this embodiment, electrode 23 is hollow and is provided with a number of ports 76 in its distal end which enable the tube to serve as a gastric tube as described in copending application Ser. No. 585,764 supra.

Figure 4:
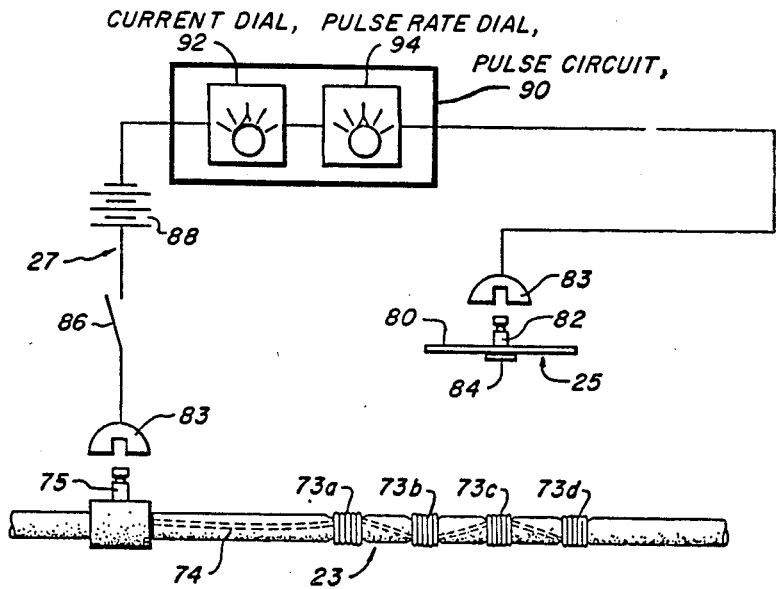
FIG. 4 is a schematic diagram of the circuit of the pacer shown in FIGS. 1 and 2.

When the electrode 23 is used to pace the heart, the distal end preferably is positioned so that the uppermost electrode contact 73a lies approximately 1½ to 2 inches beyond the balloon cuff 18 within the lower third of the esophagus. The second, external electrode 25 as shown in FIGS. 1 and 4 is used in combination with the electrode 23 to impose pulsed charges upon the patient's heart. The external electrode 25 may be like those used in electrocardiogram machines and includes a flat circular pad 80 with a post contact 82 on its upper surface connected to electrical contact 84 on its lower surface that bears a conducting gelatin designed to make good electrical contact with the subject's skin. The under surface of the pad 80 may also carry an adhesive to secure the electrode in place on the patient's chest. The post contacts 75 and 82 may be engaged by snaps 83 which connect the electrodes 23 and 25 to the electrical circuit 27. It is advantageous that the electrode 25 be placed above the sternum because there are few muscles in the sternum area which may be excited by the charge imposed across the electrodes 23 and 25. The circuit for energizing the electrodes is shown diagrammatically in the drawing and includes a switch 86, low voltage d.c. source 88 and a pulsing circuit 90. The pulse circuit may be adjusted by calibrated dial 92 so that the magnitude of the current may be changed from approximately 75 to 150 milliamps either continuously or in steps. The pulse rate may also be adjusted by calibrated dial 94 from approximately 70 to 100 pulses per minute. The duration of the pulse may be approximately 1 millisecond.

Figure 5:
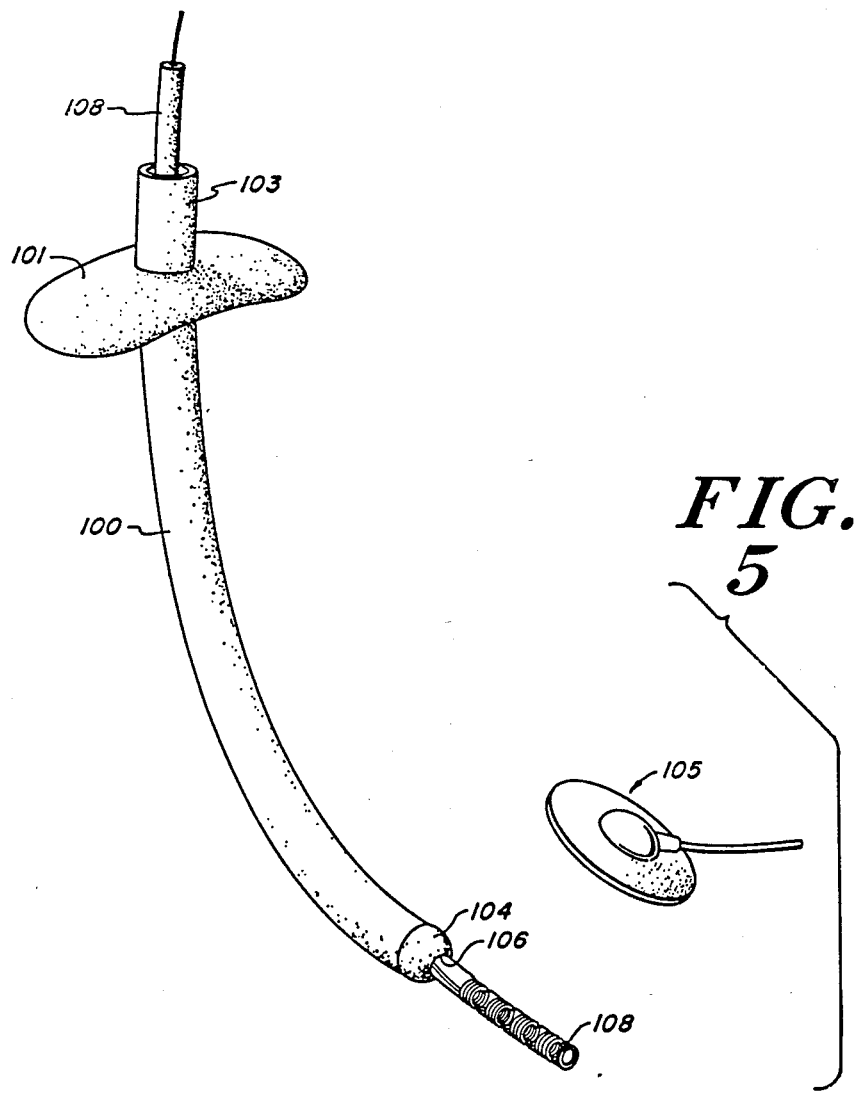
FIGS. 5 and 6 are perspective views of additional embodiments of this invention.

In FIG. 5, a simpler version of the invention is shown. In accordance with this embodiment, the apparatus is only suitable for use as a pacer and cannot be used as an airway, gastric tube, etc. In this embodiment, the apparatus includes a member 100 designed to be inserted through the mouth and throat into the esophagus in much the same fashion as the member 10 in the embodiment of FIGS. 1–3. A stop 101 is carried by the proximal end 103 of the member 100 so as to limit the depth of insertion of the member into the esophagus.

The member 100 includes a tip 104 having an opening 106 which enables the electrode 108 to be inserted through the member. The electrode 108 itself may be identical to the electrode 23 of the first embodiment. The electrode 108 in turn is used with a second electrode 105 applied externally to the body and an electrical circuit. The electrodes and circuit are identical to electrodes 23 and 25 and circuit 27 described above in connection with the first embodiment.

Figure 6:
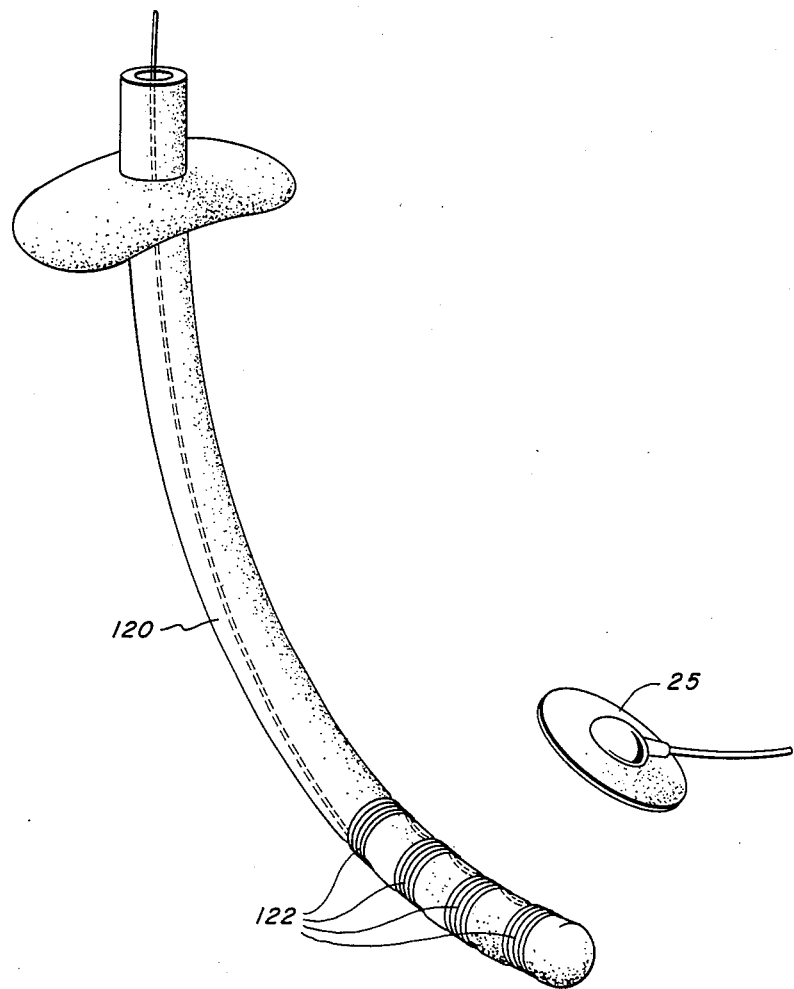

In FIG. 6, yet a more simplified embodiment of the invention is shown. In this embodiment, the electrode 120 itself is shaped to be inserted directly into the esophagus without the aid of a larger tubular member serving as a guide for that purpose as in the previously described embodiments. The electrode 120 of this embodiment carries several ring contacts 122 connected in series like the ring contacts 73 of electrodes 23 and 108. As in the other embodiments, the electrode 120 is used in combination with a second external electrode 25 applied against the sternum so as to define an electrical path through the heart. To enable the electrode to be inserted through the mouth, over the tongue and down the esophagus, it will necessarily have to possess sufficient stiffness so as not to bend or curl too easily, which would prevent insertion. The electrode body may either be solid or tubular, and the contact rings may be formed either from wire threaded through or embedded in the elongated body, or the rings may be separately formed and connected by wire conductors.

In all of the embodiments of this invention, the several contact rings on the internal electrode are each capable of defining the electrical path to the externally applied electrode to impose the timed electric pulse on the heart. The contact ring on the internal electrode which defines the path of least resistance with the electrode placed on the chest above the sternum will complete the electrical circuit.

From the foregoing description, it will be appreciated that this invention makes possible the application of a heart pacer on an emergency basis without the presence of a doctor and without the risk of infection associated with other pacers employing internal electrodes. No caratoid cut down or other surgical procedure is required to apply the electrodes to the patient. Rather, one electrode is merely applied externally to the patient's chest in the region of the sternum, and the other is inserted into the esophagus either directly or through an airway. In either case, the procedure may be carried out by a paramedic wherever the patient may be. Because no surgery is required to install the pacer, it may be applied very quickly, without the risks attendant to surgical procedures, to establish continous heart function at a selected rate. The internal and external electrodes establish a direct electrical path through the heart.

Having described the invention in detail, those skilled in the art will appreciate that numerous modifications may be made in it without departing from the spirit of the invention. Therefore, it is not intended that the breadth of this invention be limited to the specific embodiments illustrated and described. Rather, its scope is to be determined by the appended claims and their equivalents.

What is claimed is:

1. A method of pacing the heart of a patient to promote continuous heart function at a prescribed rate comprising the steps of:
   inserting a tubular member into the esophagus of the patient,
   inserting a first electrode through the member into the lower third of the patient's esophagus,
   placing an ECG-type electrode on the patient's body over the sternum and in contact with the patient's skin,
   providing a pulse circuit with a low voltage d.c. source for producing a pacing current within the approximate range of 75 to 150 milliamps and within the approximate rate of 70 to 100 pulses per minute,
   and connecting the circuit to the electrodes to cause the pulsing current to flow between the electrodes and through the heart for pacing the heart.

2. A method as defined in claim 1 further characterized by sealing the esophagus from the stomach above the first electrode when the electrode is in the esophagus.

3. A method of pacing a patient's heart comprising the steps of:
   placing a first electrode having at least one contact interanlly in the lower third of the patient's esophagus,
   placing a second electrode having an ECG-type contact externally on the patient's chest over the sternum with the contact in electrical communication with the patient's skin,
   and directing a pulsed pacing current between the contacts of the first and second electrodes of approximately 75 to 150 milliamps at a pulse rate of approximately 70 to 100 per minute.

4. Medical apparatus for pacing the heart comprising:
   an elongated, esophageal tubular member having distal and proximal ends for insertion of said distal end into the esophagus above the lower portion thereof,
   a passage in the member extending from the proximal to and through the distal end,
   means including a first electrode for insertion through the passage and beyond the distal end of the member and having a plurality of spaced contacts to lie below the distal end of the member in the lower portion of the esopagus,
   a second electrode for placement externally on the body of the patient over the sternum with an ECG-type contact in electrical contact with the skin,
   and a pulsing circuit having a low voltage d.c. source and a current of approximately 75–150 milliamps at a rate of approximately 70–100 pulses per minute connected across the electrodes for impressing a continuous, controlled, pulsed charge to the heart for pacing.

5. Medical apparatus as defined in claim 4 further characterized by said member having an inflatable cuff around it distal end and means connected to the cuff for inflating it to seal to upper portion of the esophagus from the stomach.

6. Medical apparatus as defined in claim 5 further characterized by means provided in the member allowing ventilating gas to be directed through the member to the respiratory passages of the patient.

7. Medical apparatus as defined in claim 5 further characterized by said member having a tip at the distal end for guiding the member into the esophagus, and an opening in the tip through which the first electrode extends to reach the lower portion of the esophagus.

8. Medical apparatus as defined in claim 4 further characterized by a hollow tube forming part of the first electrode, and a plurality of openings in the end of the tube lying in the lower portion of the esophagus when the first electrode is in place to relieve pressure in the lower portion of the esophagus.

9. Medical apparatus comprising:

an elongated, hollow, tubular member for insertion into the esophagus and having distal and proximal ends, said distal end carrying a tip which facilitates inserting the member in the esophagus, an inflatable cuff surrounding the member adjacent its distal end for sealing the lower portion of the esophagus and the stomach from the patient's respriratory passages when the cuff is inflated, a mask attached to the member at its proximal end and having a collar for sealing against the patient's face, the proximal end of said member extending through and to the outside of the mask, a plurality of holes in the wall of the member and communicating with the patients; respriatory passages when the member is in the esophagus, means including a duct extending through the member and connected to the cuff for inflating it to seal the respiratory passages of the patient from the stomach, an elongated electrode member for insertion into the first-recited member from outside the mask, with the distal end of the electrode member lying in the lower portion of the esophagus, a plurality of spaced apart electrical contacts carried by the electrode member at the distal end, a second electrode having an ECG-type contact for placement over the sternum of the patient external of the body, and a circuit connected to the electrode for imposing a low voltage across the electrodes and passing a pulsed, pacing current between the first and second electrodes and through the heart of approximately 75 to 150 milliamps at the rate of approximately 70 to 100 pulses per minute for pacing the heart.

10. Medical apparatus as defined in claim 9 further characterized by said elongates electrode member having vent means adjacent the spaced contacts for relieving pressure in the lower portion of the esophagus.

11. Medical apparatus for pacing the heart of a subject comprising an elongated electode member for insertion into the esophagus of the subject, a plurality of spaced apart electrical contacts on the member for location in the lower third of the subject's esophagus when the member is inserted, a second electrode member having an ECG-type contact for placement externally on the body of subject in contact with the skin over the sternum, a pulse circuit including a low voltage source, and means connecting the circuit to the electrode members for directing a pulsing current of approximately 75–150 milliamps between the electrodes and through the heart.

12. Medical apparatus as defined in claim 11 further characterized by said electrical contacts on the elongated electrode member being ring contacts spaced longitudinally on said member.

13. Medical apparatus as defined in claim 11 further characterized by said pulse circuit including means for varying the magnitude and pulse raate of the current.

* * * * *